United States Patent
Kumar et al.

(10) Patent No.: US 7,230,129 B2
(45) Date of Patent: Jun. 12, 2007

(54) PROCESS FOR THE PREPARATION OF OPTICALLY PURE ISOMERS OF 2-(4-HYDROXY PHENOXY)-2-METHYL-BUTYRIC ACID METHYL ESTER

(75) Inventors: Potlapally Rejender Kumar, Hyderabad (IN); Velagala V. R. M. K. Reddy, Hyderabad (IN); Jangalgar Tirupathy Reddy, Hyderabad (IN); Gurram Ranga Madhaven, Hyderabad (IN); Sunil Kumar Singh, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 11/247,490

(22) Filed: Oct. 11, 2005

(65) Prior Publication Data

US 2006/0194980 A1     Aug. 31, 2006

(30) Foreign Application Priority Data

Oct. 11, 2004   (IN)   .................. 1050/CHE/2004

(51) Int. Cl.
*C07C 69/76* (2006.01)
(52) U.S. Cl. ....................................... 560/55
(58) Field of Classification Search ............... 560/55
See application file for complete search history.

(56) References Cited

OTHER PUBLICATIONS

Shi, Yao-Jun; Hughes, David L.; McNamara, James M Stereospecific synthesis of chiral tertiary alkylaryl ethers via Mitsunobu reaction with complete inversion of configuration. Tetrahedron Letters (2003), 44(18), 3609-3611.*

* cited by examiner

*Primary Examiner*—Thurman K. Page
*Assistant Examiner*—MLouisa Lao
(74) *Attorney, Agent, or Firm*—Milagros A. Cepeda; Robert A. Franks

(57) ABSTRACT

The invention provides a process for preparing R-(+)-2-(4-hydroxyphenoxy)-2-methyl-butyric acid methyl ester of the formula (I):

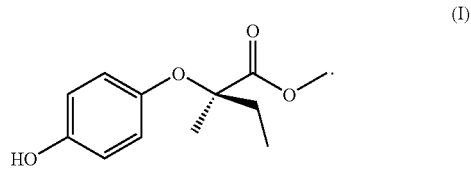

(I)

Various embodiments and variants are provided.

The invention also provides a process for preparing S-(−)-2-(4-hydroxyphenoxy)-2-methyl-butyric acid methyl ester of the formula (II)

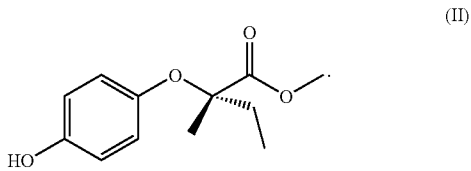

(II)

Various embodiments and variants are provided.

39 Claims, No Drawings

PROCESS FOR THE PREPARATION OF OPTICALLY PURE ISOMERS OF 2-(4-HYDROXY PHENOXY)-2-METHYL-BUTYRIC ACID METHYL ESTER

CROSS-REFERENCE TO RELATED APPLICATIONS

This application claims priority to Indian Patent Application No. 1050/CHE/2004, filed Oct. 11, 2004, the contents of which are incorporated by reference in their entirety.

BACKGROUND

The compounds of the formula (I) and the formula (II) are useful as intermediates for the preparation of certain pharmaceutically-active compounds:

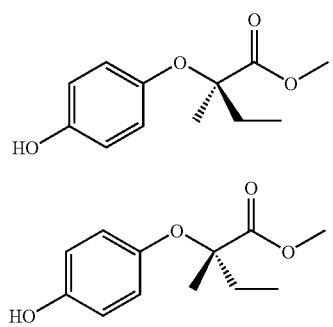

These compounds are useful for the preparation of compounds of the formula (III) disclosed in the pending international application number PCT/IB2004/000208:

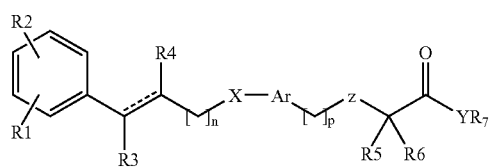

There exists a continuing need for developing a process for the preparation of the compound of formula (I) and formula (II).

SUMMARY

In accordance with one aspect, the invention provides a process for preparing R-(+)-2-(4-hydroxyphenoxy)-2-methyl-butyric acid methyl ester of the formula (I):

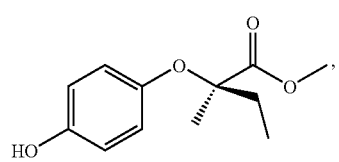

the process including: a) reacting (RS)-2-(4-arylalkoxyphenoxy)-2-methyl-butyric acid with R-(−)-arylglycinol; and b) converting the resulting R-arylglycinol salt of 2-(4-arylalkoxyphenoxy)-2-methyl-butyric acid to R-(+)-2-(4-hydroxyphenoxy)-2-methyl-butyric acid methyl ester of the formula (I). Various embodiments and variants of this aspect of the invention are provided.

In accordance with another aspect, the invention provides a process for preparing S-(−)-2-(4-hydroxyphenoxy)-2-methyl-butyric acid methyl ester of the formula (II)

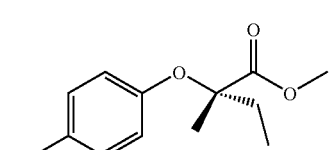

the process including: a) reacting (RS)-2-(4-arylalkoxyphenoxy)-2-methyl-butyric acid with S-(+)-arylglycinol; and b) converting the resulting S-arylglycinol salt of 2-(4-arylalkoxyphenoxy)-2-methyl-butyric acid to S-(−)-2-(4-hydroxyphenoxy)-2-methyl-butyric acid methyl ester of the formula (II). Various embodiments and variants of this aspect of the invention are provided.

DETAILED DESCRIPTION

U.S. Pat. No. 3,795,691, and International Publications Nos. WO 03/059875 A2, WO2004/056355 A1 have disclosed the compound of formula (I) generically but did not provide a specific example for its preparation. International Publication No. WO 2004010992 has disclosed the resolution of (R) and (S) isomers from the racemic methyl 2-(4-hydroxyphenoxy)-2-methylbutanoate by the use of high pressure liquid chromatography (HPLC).

The present invention provides a process for the preparation of substantially optically pure (R) and (S) isomers of 2-(4-Hydroxy phenoxy)-2-methyl-butyric acid methyl esters of the formula (I) and formula (II):

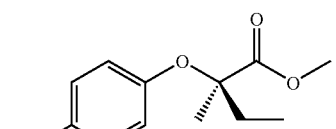

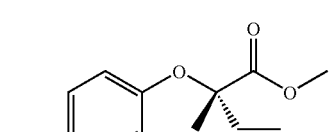

According to one aspect, there is provided a process for the preparation of the compound of the formula (I), an embodiment of which process is illustrated in Scheme I:

Scheme I

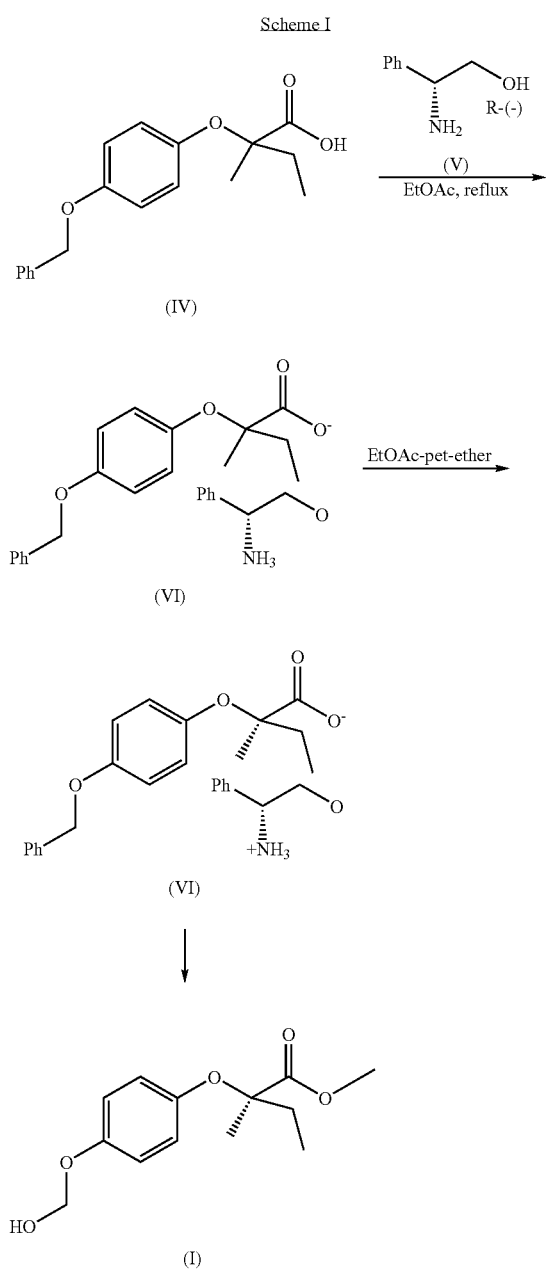

With reference to Scheme I, (RS)-2-[4-phenylmethoxyphenoxy]-2-methyl butyric acid of the formula (IV) is reacted with R-(−)-phenylglycinol of the formula (V) in the presence of a solvent, non-limiting examples of which include ethyl acetate, ether, acetone, chloroform, chlorobenzene, dichloroethane or mixtures thereof, to produce diastereomeric R-phenylglycinol salt of the formula (VI). The reaction is carried out in the temperature from about 20° C. to about 80° C. for a period of from about 1 to about 14 hours. The p-phenylmethoxy derivative of the formula (IV) may be replaced with other arylalkoxy derivatives of 2-[4-substituted-phenoxy]-2-methyl-butyric acid, examples of which include tolylmethoxy and phenylethoxy, but (RS)-2-[4-phenylmethoxyphenoxy]-2-methyl butyric acid is preferred. Likewise, R-phenylglycinol may be replaced with other R-aryl glycinols, but R-phenylglycinol is preferred.

The reaction between (RS)-2-[4-phenylmethoxyphenoxy]-2-methyl butyric acid and R-(−)-phenylglycinol provides a diastereomeric mixture of R-phenylglycinol salt of R-2-(4-phenylmethoxyphenoxy)-2-methyl-butyric acid and R-phenylglycinol salt of S-2-(4-phenylmethoxyphenoxy)-2-methyl-butyric acid, which is separated in a suitable solvent, preferred examples of which include ethyl acetate, petroleum ether and mixtures thereof. Fractional crystallization may be carried out from 2 to about 8 times to obtain substantially pure compound of the formula (VI).

The purified R-salt of the formula (VI) is then converted to the desired (R)-2-(4-hydroxy phenoxy)-2-methyl-butyric acid methyl ester of the formula (I) by an action of a mineral acid, non-limiting examples of which include sulfuric acid and hydrochloric acid. Preferably, the reaction is carried out in methanol, in the presence of a sufficient acid concentration to convert the phenylglycinol salt to the carboxylic acid, to esterify the carboxylic acid to its methyl ester, and to deprotect the hydroxyl group in the para-position of the benzyl ring. The temperature of reaction is from about 40° C. to about 105° C. The time of the reaction is from about 1 hour to about 15 hours.

Another embodiment is illustrated in the Scheme II:

Scheme II

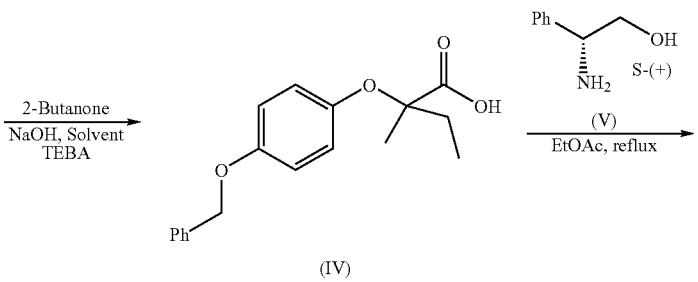

-continued

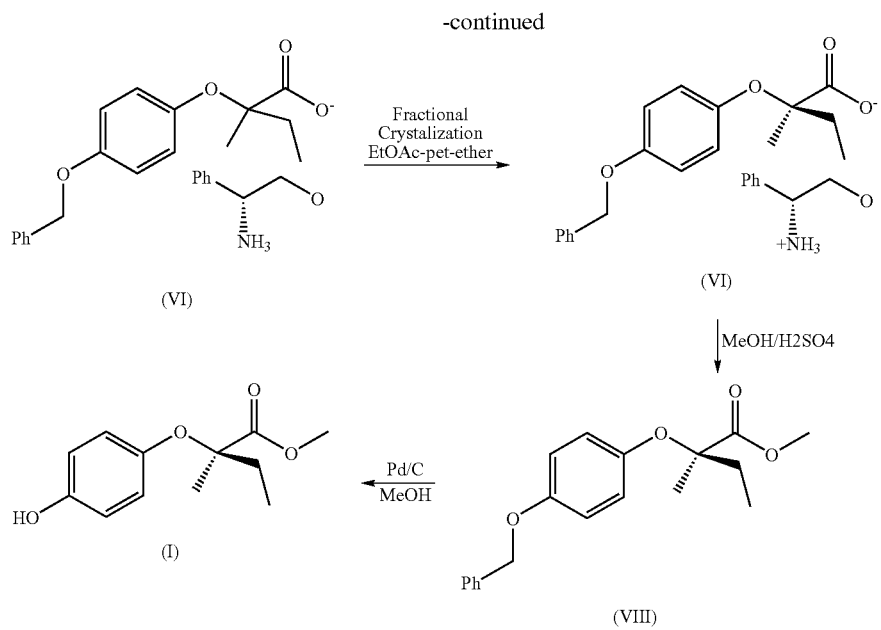

To provide the racemate of the formula (IV), 4-benzyloxyphenol of the formula VII is reacted with 2-butanone in the presence of a solvent, a base and a catalyst, such as triethylbenzylammoniumchloride. Examples of suitable solvents include toluene, benzene, xylene and mixtures thereof. Examples of suitable bases include anhydrous alkali metal hydroxide and alkali metal carbonate such as sodium hydroxide, potassium hydroxide, sodium carbonate, potassium carbonate. The temperature of reaction is from about 15° C. to about 70° C. The time of the reaction is from about 8 hours to about 17 hours.

As in the embodiment described in reference to Scheme I, the racemate is reacted with R-(−)-phenylglycinol of the formula (V) to produce a diastereomeric mixture of R-(−)-phenylglycinol salts of 2-[4-phenylmethoxyphenoxy]-2-methyl butyric acid. The reaction solvent is chosen form ethyl acetate, ether, acetone, chloroform, chlorobenzene, dichloroethane and a mixture thereof. The reaction is carried out in the temperature from about 20° C. to about 80° C. for a period of 1 to 14 hours. The mixture is purified by fractional crystallizations in suitable solvent, such as ethyl acetate, petroleum ether and mixtures thereof, to separate and isolate the R-diastereomer. Fractional crystallization may be performed from 2 times to about 8 times to get substantially optically pure compound of formula (VI).

The next step is the esterification of the compound, which is carried out in the presence of a mineral acid such as sulfuric acid, hydrochloric acid and solvent such as an alcohol to produce an ester. Other esters besides methyl ester are contemplated. Alcohol may be selected from methanol, ethanol, propanol, iso propanol, n-butanol, t-butanol and others, although methanol is preferred to obtain the compound of the formula (I). The R-diastereomer is esterified to a methyl ester of the formula (VIII) in the presence of methanol and a mineral acid. The temperature of the reaction is from about 10° C. to about 100° C. The time of the reaction is from about 10 to about 18 hours.

Finally, the compound of formula (VIII) is deprotected in the presence of a noble metal catalyst, a alcohol, and ammonium formate to produce the compound of formula (I). Examples of suitable catalysts include platinum, palladium, rhodium, platinum on carbon (Pt/C), palladium on carbon (Pd/C) and mixtures thereof. Examples of suitable alcohols include methanol, ethanol, propanol, isopropanol, n-butanol, t-butanol and mixtures thereof. The temperature of the reaction is from about 55° C. to about 105° C. The time of the reaction is from about 20 minutes to about 2 hours.

According to another aspect, the invention provides a process for the preparation of the compound of the formula (II), an embodiment of which process is illustrated in Scheme III:

Scheme III

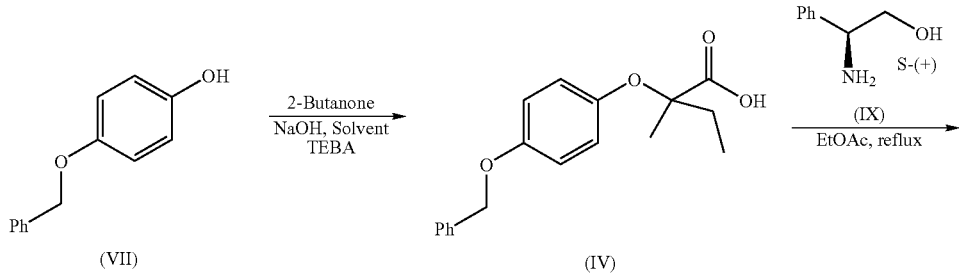

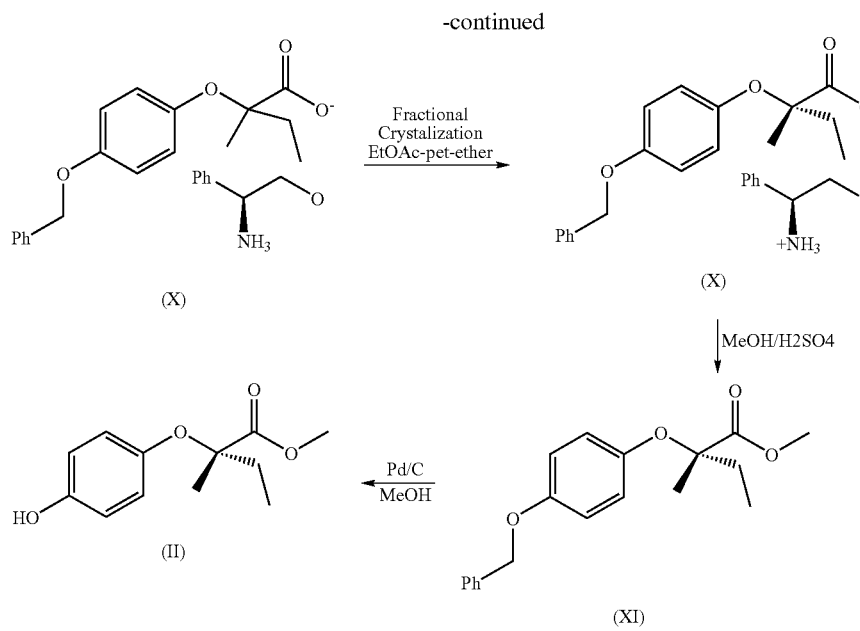

With reference to Scheme III, the racemate of the formula (IV) may provided in the same manner as described above. 4-benzyloxyphenol of the formula VII is reacted with 2-butanone in the presence of solvent, base and catalyst, such as triethylbenzylammoniumchloride, to produce (RS)-2-[4-phenylmethoxyphenoxy]-2-methyl butyric acid of the formula (IV). Examples of suitable solvents include toluene, benzene, xylene and mixtures thereof. Examples of suitable bases include anhydrous alkali metal hydroxide and alkali metal carbonate such as sodium hydroxide, potassium hydroxide, sodium carbonate, and potassium carbonate. The temperature of reaction is from about 15° C. to about 70° C. The time of the reaction is from about 8 hours to about 17 hours.

The compound of the formula (IV) is then reacted with S-(+)-phenylglycinol of the formula (IX), in the presence of a suitable solvent, to produce the compound of the formula (X). Examples of suitable solvents include ethyl acetate, ether, acetone, chloroform, chlorobenzene, and dichloroethane. Ethylacetate is preferred. The temperature of reaction is in the range of 20° C. to 80° C. The time of reaction is in the range of 1 to 14 hours.

The reaction between (RS)-2-[4-phenylmethoxyphenoxy]-2-methyl butyric acid and S-(+)-phenylglycinol provides a diastereomeric mixture of S-phenylglycinol salt of R-2-(4-phenylmethoxyphenoxy)-2-methyl-butyric acid and S-phenylglycinol salt of S-2-(4-phenylmethoxyphenoxy)-2-methyl-butyric acid, which is separated in a suitable solvent, preferred examples of which include ethyl acetate, petroleum ether and mixtures thereof. Fractional crystallization may be carried out from 2 to about 8 times to obtain substantially pure compound of the formula (X) (S-phenylglycinol salt of S-2-(4-phenylmethoxyphenoxy)-2-methyl-butyric acid).

The next step is esterification of the compound of formula (X), which is carried out in the presence of a mineral acid such as sulfuric acid, hydrochloric acid and solvent such as an alcohol to produce a compound of the formula (XI). Other esters besides methyl ester are contemplated. Alcohol may be selected from methanol, ethanol, propanol, iso propanol, n-butanol, t-butanol and others, although methanol is preferred to obtain the compound of the formula (II). The temperature of reaction is at 10° C. to 50° C. The time of the reaction is 10 to 18 hours.

i. Deprotection of the compound of formula (XI) is carried out in the presence of alcohol, noble metal catalyst and ammonium formate to produce the compound of formula (II). Suitable alcohols include methanol, ethanol, propanol, isopropanol, n-butanol, t-butanol and the like. The noble metal catalyst is selected form Platinum, Palladium, Rhodium, Platinum on carbon (Pt/C), Palladium on carbon (Pd/C) or mixture thereof. The temperature of reaction is at 55° C. to 105° C. The time of the reaction is 20 mins to 2 hours.

The invention is explained in detail in the examples given below which are provided by way of illustration only and therefore should not be construed to limit the scope of the invention.

EXAMPLE-1

Preparation of R-(+)-2-Hydroxyphenoxy-2-methyl butyric acid methyl ester

Step-1:

Preparation of Diastereomeric R-(−)-phenylglycinol salt of (RS)-2-[4-phenylmethoxyphenoxy]-2-methyl butyric acid and its resolution

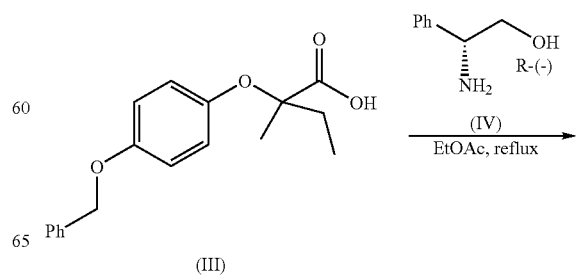

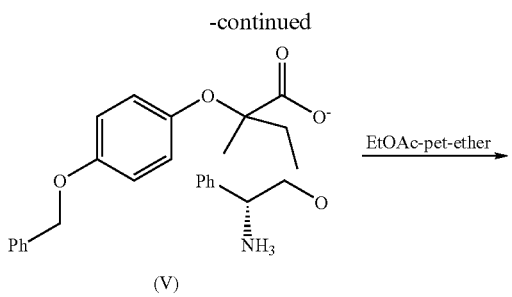

(V)

EtOAc-pet-ether →

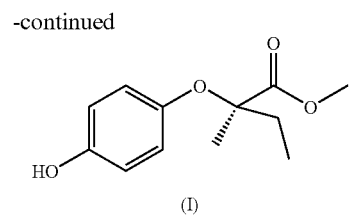

(I)

The compound of formula (VI) (10.0 grams, 0.22 mol) was dissolved in methanol (150 mL) and conc. sulphuric acid (10.0 mL) was drop-wise added under stirring at 25 to 35° C. Refluxed the reaction mixture 9 to 15 hours. Additional conc. sulphuric acid (10.0 mL) was added and further refluxed for 4–5 hours. Cooled the reaction mixture to 25 to 32° C., poured over ice-water and extracted with EtOAc. The organic layer was washed with water, dried (anhyd. Sodium sulphate) and the solvent was evaporated. The coloured gummy mass was purified by column chromatography using 230–400 mesh silica gel and eluting with a mixture of ethyl acetate and petroleum ether (90:10) to get a white-coloured thick liquid of the desired compound (4.5 grams, 88%). IR (Neat) 3422, 2979, 2950, 2883, 1734, 1508, 1447, 1378 cm$^{-1}$. $^1$H NMR (200 MHz, CDCl$_3$) δ 6.78 (dd, J=7.6 & 2.6 Hz, 2H, Ar H), 6.68 (dd, J=7.6 & 2.6 Hz, 2H, Ar H), 4.80 (bs, 1H, D$_2$O exchangeable), 3.77 (s, 3H), 1.95 (q, J=7.2 Hz, 2H), 1.41 (s, 3H), 0.97 (t, J=7.2 Hz, 3H). MS (Cl Method) 224 (M$^+$), 193, 165, 110. HPLC (chemical) 98.95% [column: altima C-18; mobile phase: 0.01 M KH$_2$PO$_4$: CH$_3$CN; UV: 225 nm]. HPLC (chiral) 99.49% [column: chiralpak ADH; mobile phase: Hexane:IPA:TFA (94:06:0.3); UV: 225 nm]. [α]$^{26}_D$ +35.7 (c=1.0%, MeOH).

(RS)-2-[4-phenylmethoxyphenoxy]-2-methyl butyric acid (180.0 g, 0.6 mol), dissolved in ethylacetate (1.8 L), was warmed to 50–60° C. and R-(−)-phenylglycenol (74.0 grams, 0.54 mol) was slowly added. A solid started separating during addition. After heating at this temperature for 2 hours, the whole mass was stirred for 9 to 15 hours at 25–35° C. and filtered. The solid so obtained was subjected to four consecutive fractional crystallizations with a mixture of ethylacetate and petroleum ether (5:3; 8.0 vol. each). No clear solution was observed during heating. The slurry was refluxed for 30 minutes in every crystallization and was always filtered after stirring at room temperature for 30 minutes. Wt: 86.0 g.

IR (KBr) 3421, 2936, 1568, 1507, 1457, 1386, 1224 cm$^{-1}$. $^1$H NMR (200 MHz, DMSO-d$_6$) δ 7.44–7.29 (m, 10H), 6.85 (dd, J=9.4 & 2.2 Hz, 2H, Ar H), 6.75 (dd, J=9.4 & 2.2 Hz, 2H, Ar H), 5.00 (s, 2H), 4.08–4.02 (m, 1H), 3.58–3.42 (m, 2H), 2.50 (bs, D$_2$O exchangeable, 2H), 1.78 (q, J=7.8 Hz, 2H), 1.29 (s, 3H), 0.87 (t, J=7.4 Hz, 3H). MS (EI Method) 300, 255, 200, 138, 106. HPLC (chiral) 98.73% [column: chiralpak ADH; mobile phase: Hexane:IPA:TFA (94:06:0.3); UV: 225 nm].

Step-2:

Preparation of R-(+)-2-Hydroxyphenoxy-2-methyl butyric acid methyl ester

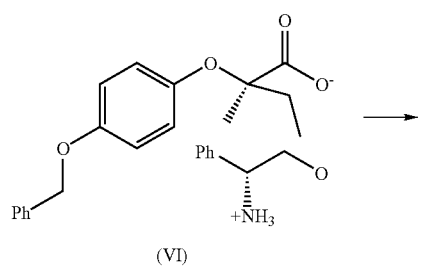

(VI)

→

EXAMPLE-2

Preparation of (+)-methyl-2-(4-hydroxyphenoxy)-2-methyl butyrate

Step-1:

Preparation of 2-[4-phenyl-methoxyphenoxy]-2-methyl butyric acid

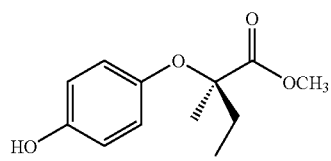

To the 4-benzyloxyphenol (40 grams, 0.2 mol) add toluene (400 mL) and sodium hydroxide (powdered) (64 grams, 1.6 mol) at 25–30° C., stirred for 30 minutes and then added 2-butanone (180 mL, 2 mol) for 20 minutes drop wise. To the reaction mixture added triethylbenzylammoniumchloride (4 grams) in one portion and the mixture was stirred for 10 minutes. Chloroform (66 mL, 0.8 mol) was added at 25–30° C. very slowly for 30 to 45 minutes by controlling the reaction mixture temperature by cooling intermittently with ice bath, to maintain the temperature below 45° C. The reaction mixture was stirred at 25–30° C. for 13 to 14 hours. The mixture was poured in to water (500 mL) and separated the organic and aqueous layers. The aqueous layer was washed with toluene thrice to remove impurities formed in the reaction. The aqueous layer was acidified (pH to 2) and extracted with ethyl acetate. The organic layer was washed with water, brine and dried over sodium sulphate, and evaporated to get a solid, which was titrated with n-hexane to get 2-[4-phenyl-methoxyphenoxy]-2-methyl butyric acid as a pale yellow solid. (18.8 grams, 32%); Melting Point: 50–55° C.

$^1$H NMR (CDCl$_3$, 400 MHz): δ 7.43–7.30 (m, 5H), 6.92 (d, J=9.13 Hz, 2H), 6.88 (d, J=9.13 Hz, 2H), 5.02 (s, 2H), 2.00–1.83 (m, 2H), 1.42 (s, 3H), 1.05 (t, J=7.53 Hz, 3H). Mass (m/z): 301 (M+1).

Step-2:

Preparation of (+)-2-[4-phenyl-methoxyphenoxy]-2-methyl butyric acid

2-[4-Phenyl-methoxyphenoxy]-2-methyl butyric acid (18.8 grams, 62.67 mmol), obtained in step (i), was converted to its R(−)phenylglycinol salt by stirring with the R(−)phenylglycinol (7.7 grams, 56.4 mmol) in ethyl acetate (100 mL) at 25–30° C. for 5 hours to get a suspension of white solid, which was filtered and dried under vacuum to get a racemic acid salt. The resultant salt was recrystallised in ethyl acetate for 3 to 4 times to get a chirally pure (+)enantiomeric salt of 2-[4-phenyl-methoxyphenoxy]-2-methyl butyric acid. The salt was released by treating it with 25% sulphuric acid and extracting it in to ethyl acetate. The ethyl acetate layer was washed with water and dried over sodiumsulphate to give pure (+)-2-[4-phenyl-methoxyphenoxy]-2-methyl butyric acid as white solid (5.2 grams, 43%). Melting Point: 80–82° C. $^1$H NMR (CDCl$_3$, 400 MHz): δ 7.42–7.30 (m, 5H), 6.91 (d, J=9.13 Hz, 2H), 6.88 (d, J=9.13 Hz, 2H), 5.02 (s, 2H), 2.03–1.82 (m, 2H), 1.42 (s, 3H), 1.05 (t, J=7.52 Hz, 3H). Mass (m/z): 300 (M+).

Step-3:

Preparation of (+)-methyl-2-[4-phenyl-methoxyphenoxy]-2-methyl butyrate

To the (+)-2-[4-phenyl-methoxyphenoxy]-2-methyl butyric acid (5.2 grams, 17.35 mmol), obtained in step (ii), added methanol (50 mL) and catalytic amount of concentrated sulphuric acid (1 mL) and refluxed for 14 hours. Reaction mixture was cooled to 25–30° C. and the methanol was evaporated and the residue was dissolved in ethyl acetate, washed with 10% sodiumbicarbonate solution, water and dried over sodiumsulphate. Evaporate the solvent to give oily (+)-methyl-2-[4-phenyl-methoxyphenoxy]-2-methyl butyrate (5.0 grams, 92%).

$^1$H NMR (CDCl$_3$, 200 MHz): δ 7.42–7.30 (m, 5H), 6.85 (d, J=9.41 Hz, 2H), 6.81 (d, J=9.41 Hz, 2H), 4.99 (s, 2H), 3.76 (s, 3H), 1.95–1.92 (m, 2H), 1.42 (s, 3H), 0.97 (t, J=7.53 Hz, 3H).
Mass (m/z): 314 (M$^+$).

Step-4:

Preparation of (+)-methyl-2-[4-hydroxy phenoxy]-2-methyl butyrate (+)-Methyl-2-[4-phenyl-methoxyphenoxy]-2-methyl butyrate (5.0 grams, 15.92 mmol), obtained in step (iii), was dissolved in methanol (50 mL) and added 10% palladium/charcoal (5.0 grams) and ammonium formate (2.0 grams, 31.75 mmol). Refluxed under nitrogen atmosphere for 45 minutes. The resultant mixture was cooled to 25–30° C. and filtered through celite, washed with methanol and evaporated the solvent to give (+)-methyl-2-[4-hydroxy phenoxy]-2-methyl butyrate as thick oil (3.16 grams, 90%).

$^1$H NMR (CDCl$_3$, 200 MHz): δ 6.77 (d, J=8.87 Hz, 2H), 6.69 (d, J=8.87 Hz, 2H), 3.77 (s, 3H), 2.09–1.88 (m, 2H), 1.41 (s, 3H), 0.97 (t, J=7.52 Hz, 3H).

EXAMPLE-3

Preparation of (−) methyl-2-(4-hydroxyphenoxy)-2-methyl butyrate

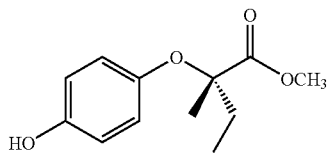

Step-1

Preparation of 2-[4-phenyl-methoxyphenoxy]-2-methyl butyric acid

To the 4-benzyloxyphenol (40 grams, 0.2 mol) add toluene (400 mL) and sodium hydroxide (powdered) (64 grams, 1.6 mol) at 25–30° C., stirred for 30 minutes and then add 2-butanone (180 mL, 2 mol) for 20 minutes drop wise. Added triethylbenzyl ammoniumchloride (4 grams) in one portion and the mixture was stirred for 10 minutes. Chloroform (66 mL, 0.8 mol) was added at 25–30° C. very slowly for 30 to 45 minutes by controlling the reaction mixture temperature by cooling intermittently with ice bath, to maintain the temperature below 45° C. Then the reaction mixture was stirred at 25–30° C. for 13 to 14 hours. The mixture was poured in to water (500 mL) and separated the organic and aqueous layers. The aqueous layer was washed with toluene thrice to remove impurities formed in the reaction. The aqueous layer was acidified (pH to 2) and extracted with ethyl acetate. The organic layer was washed with water, brine and dried over sodiumsulphate, and evaporated to get a solid, which was titrated with n-hexane to get a reasonably pure 2-[4-phenyl-methoxyphenoxy]-2-methyl butyric acid as a pale yellow solid. (18.8 grams, 32%); Melting Point: 50–55° C. $^1$H NMR (CDCl$_3$, 400 MHz): δ 7.43–7.30 (m, 5H), 6.92 (d, J=9.13 Hz, 2H), 6.88 (d, J=9.13 Hz, 2H 5.02 (s, 2H), 2.00–1.83 (m, 2H), 1.42 (s, 3H), 1.05 (t, J=7.53 Hz, 3H). Mass (m/z): 301 (M+1).

Step-2:

Preparation of (−)-2-[4-phenyl-methoxyphenoxy]-2-methyl butyric acid

2-[4-Phenyl-methoxyphenoxy]-2-methyl butyric acid (18.8 grams, 62.67 mmol), obtained in step (i), was converted to its S(+)phenylglycenol salt by stirring with the S(+)phenylglycenol (7.7 grams, 56.4 mmol) in ethyl acetate (100 mL) at 25–30° C. for 5 hours to get a suspension of white solid, which was filtered and dried under vacuum to get a salt. This salt of racemic acid was recrystallised in ethyl acetate for 3 to 4 times to get a chirally pure (−)enantiomeric salt of 2-[4-phenyl-methoxyphenoxy]-2-methyl butyric acid. The resultant salt was released by treating it with 25% sulphuric acid and extracting it in to ethyl acetate. The ethyl acetate layer was washed with water and dried over sodiumsulphate to give (−)-2-[4-phenyl-methoxyphenoxy]-2-methyl butyric acid as a pure white solid. (5.2 grams, 43%). Melting Point: 80–82° C. $^1$H NMR (CDCl$_3$, 400 MHz): δ 7.42–7.30 (m, 5H), 6.91 (d, J=9.13 Hz, 2H), 6.88 (d, J=9.13 Hz, 2H), 5.02 (s, 2H), 2.03–1.82 (m, 2H), 1.42 (s, 3H), 1.05 (t, J=7.52 Hz, 3H).

Mass (m/z): 300 (M+).

Step-3:

Preparation of (−)-methyl-2-[4-phenyl-methoxyphenoxy]-2-methyl butyric acid

To the (−)-2-[4-phenyl-methoxyphenoxy]-2-methyl butyric acid (5.2 grams, 17.35 mmol), obtained in step (ii), methanol (50 mL) and catalytic amount of concentrated sulphuric acid (1 mL) was added and refluxed for 14 hours. Reaction was cooled to 25–30° C. and the methanol was evaporated. The residue was dissolved in ethylacetate, washed with 10% sodium bicarbonate solution, water and dried over sodium-sulphate, evaporated the solvent to give oily (−)-methyl-2-[4-phenyl-methoxyphenoxy]-2-methyl butyrate (5.0 grams, 92%).

$^1$H NMR (CDCl$_3$, 200 MHz): δ 7.42–7.30 (m, 5H), 6.85 (d, J=9.41 Hz, 2H), 6.81 (d, J=9.41 Hz, 2H), 4.99 (s, 2H), 3.76 (s, 3H), 1.95–1.92 (m, 2H), 1.42 (s, 3H), 0.97 (t, J=7.53 Hz, 3H). Mass (m/z): 314 (M$^+$).

Step-4:

Preparation of (−)-methyl-2-[4-hydroxy phenoxy]-2-methyl butyrate (−)-Methyl-2-[4-phenyl-methoxyphenoxy]-2-methyl butyrate (5.0 grams, 15.92 mmol), obtained in step (iii), was dissolved in ethanol (50 mL). Added 10% palladium/charcoal (5.0 grams) and ammoniumformate (2.0 grams, 31.75 mmol). Refluxed under nitrogen atmosphere for 45 minutes. The resultant mixture was cooled to 25–30° C. and filtered through celite, washed with methanol and evaporated the solvent to give (−)-methyl-2-[4-hydroxy phenoxy]-2-methyl butyrate as thick oil (3.16 grams, 90%). $^1$H NMR (CDCl$_3$, 200 MHz); δ 6.77 (d, J=8.87 Hz, 2H), 6.69 (d, J=8.87 Hz, 2H), 3.77 (s, 3H), 2.09–1.88 (m, 2H), 1.4 (s, 3H), 0.97 (t, J=7.52 Hz, 3H).

We claim:

1. A process for preparing R-(+)-2-(4-hydroxyphenoxy)-2-methyl-butyric acid methyl ester of the formula (I):

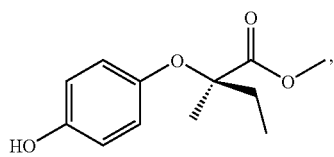

(I)

said process consisting essentially of the steps:
 a) reacting (RS)-2-(4-arylalkoxyphenoxy)-2-methyl-butyric acid with R-arylglycinol;
 b) converting the resulting R-arylglycinol salt of (RS)-2-(4-arylalkoxyphenoxy)-2-methyl-butyric acid into said R-(+)-2-(4-hydroxyphenoxy)-2-methyl-butyric acid methyl ester of the formula (I).

2. The process of claim 1, wherein said (RS)-2-(4-arylalkoxyphenoxy)-2-methyl-butyric acid is (RS)-2-(4-phenyl-methoxyphenoxy)-2-methyl-butyric acid.

3. The process of claim 1, wherein said R-(+)-2-(4-hydroxyphenoxy)-2-methyl-butyric acid methyl ester is substantially free of its corresponding (S) isomer.

4. The process of claim 2, wherein said R-(−)-arylglycinol is R-(−)-phenylglycinol.

5. The process of claim 4, wherein said reacting step a) is carried out in a solvent chosen from ethyl acetate, ether, acetone, chloroform, chlorobenzene, dichloroethane and mixtures thereof.

6. The process of claim 4, wherein said reacting step a) is carried out at a temperature ranging from about 20° C. to about 80° C.

7. The process of claim 4, consisting essentially of separating R-phenylglycinol salt of (R)-2-(4-phenylmethoxyphenoxy)-2-methyl-butyric acid from R-phenylglycinol salt of (S)-2-(4-phenylmethoxyphenoxy)-2-methyl-butyric acid.

8. The process of claim 7, wherein the separating step comprises fractional crystallization.

9. The process of claim 8, wherein said fractional crystallization is carried out in a solvent chosen from ethyl acetate, petroleum ether and mixtures thereof.

10. The process of claim 7, wherein said converting step b) comprises converting said R-phenylglycinol salt of R-2-(4-phenylmethoxyphenoxy)-2-methyl-butyric acid to said R-(+)-2-(4-hydroxyphenoxy)-2-methyl-butyric acid methyl ester.

11. The process of claim 10, wherein said converting step b) treating said R-phenylglycinol salt of R-2-(4-phenylmethoxyphenoxy)-2-methyl-butyric acid with a mineral acid in the presence methanol.

12. The process of claim 11, wherein said converting step b) is carried out in a single reacting vessel procedure.

13. The process of claim 11, wherein the mineral acid is chosen from sulfuric acid and hydrochloric acid.

14. The process of claim 11, wherein said converting step is carried out at a temperature from about 40° C. to about 105° C.

15. The process of claim 11, wherein said converting step is carried out for a period of from about 1 hour to about 15 hours.

16. The process of claim 4, further comprising providing said 2-(4-phenylmethoxyphenoxy)-2-methyl-butyric acid by reacting 4-benzyloxyphenol with 2-butanone in the presence of a solvent, a base and a catalyst.

17. The process of claim 16, wherein the catalyst is triethylbenzylammoniumchloride.

18. The process of claim 10, wherein said converting step b) comprises i) reacting said R-phenylglycinol salt of R-2-(4-phenylmethoxyphenoxy)-2-methyl-butyric acid with an external acid to obtain a methyl ester of R-2-(4-phenylmethoxyphenoxy)-2-methyl-butyric acid, and ii) converting said methyl ester to said R-(+)-2-(4-hydroxyphenoxy)-2-methyl butyric acid.

19. The process of claim 17, wherein said external acid is chosen from sulfuric acid and hydrochloric acid.

20. The process of claim 17, wherein the step ii) is carried out in the presence of a noble metal catalyst.

21. The process of claim 19, wherein the noble metal catalyst is chosen from platinum, palladium, rhodium, platinum on carbon, palladium on carbon and mixtures thereof.

22. The process of claim 19, wherein the step b) is carried out in the presence of methanol and ammonium formate.

23. A process for preparing S-(−)-2-(4-hydroxyphenoxy)-2-methyl-butyric acid methyl ester of the formula (II):

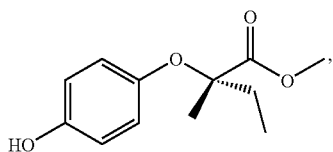

(II)

said process consisting essentially of the steps:
a) reacting (RS)-2-(4-arylalkoxyphenoxy)-2-methyl-butyric acid with S-(+)-arylglycinol;
b) converting the resulting S-arylglycinol salt of (RS)-2-(4-phenylmethoxyphenoxy)-2-methyl-butyric acid into said S-(−)-2-(4-hydroxyphenoxy)-2-methyl-butyric acid methyl ester of the formula (II).

24. The process of claim 23, wherein said (RS)-2-(4-arylalkoxyphenoxy)-2-methyl-butyric acid is (RS)-2-(4-phenyl methoxyphenoxy)-2-methyl-butyric acid.

25. The process of claim 23, wherein said S-(−)-2-(4-hydroxyphenoxy)-2-methyl-butyric acid methyl ester is substantially free of its corresponding (R) isomer.

26. The process of claim 24, wherein said S-(−)-arylglycinol is S-(−)-phenylglycinol.

27. The process of claim 23, wherein said step a) is carried out in a solvent chosen from ethyl acetate, ether, acetone, chloroform, chlorobenzene, dichloroethane and mixtures thereof.

28. The process of claim 23, wherein said step a) is carried out at a temperature ranging from about 20° C. to about 80° C.

29. The process of claim 26, consisting essentially of separating S-phenylglycinol salt of (S)-2-(4-phenylmethoxyphenoxy)-2-methyl-butyric acid from S-phenylglycinol salt of (R)-2-(4-phenylmethoxyphenoxy)-2-methyl-butyric acid.

30. The process of claim 29, wherein the separating step comprises fractional crystallization.

31. The process of claim 30, wherein said fractional crystallization is carried out in a solvent chosen from ethyl acetate, petroleum ether and mixtures thereof.

32. The process of claim 29, wherein said step b) comprises converting said S-phenylglycinol salt of S-2-(4-phenylmethoxyphenoxy)-2-methyl-butyric acid to said S-(−)-2-(4-hydroxyphenoxy)-2-methyl-butyric acid methyl ester.

33. The process of claim 26, consisting essentially of providing said 2-(4-phenylmethoxyphenoxy)-2-methyl-butyric acid by reacting 4-benzyloxyphenol with 2-butanone in the presence of a solvent, a base and a catalyst.

34. The process of claim 33, wherein the catalyst is triethylbenzylammoniumchloride.

35. The process of claim 32, wherein said converting step comprises i) reacting said S-phenylglycinol salt of S-2-(4-phenylmethoxyphenoxy)-2-methyl-butyric acid with an external acid to obtain a methyl ester of S-2-(4-phenylmethoxyphenoxy)-2-methyl-butyric acid, and ii) converting said methyl ester of S-2-(4-phenylmethoxyphenoxy)-2-methyl-butyric acid to said S-(−)-2-(4-hydroxyphenoxy)-2-methyl-butyric acid.

36. The process of claim 35, wherein said external acid is chosen from sulfuric acid and hydrochloric acid.

37. The process of claim 35, wherein the step ii) is carried out in the presence of a noble metal catalyst.

38. The process of claim 37, wherein the noble metal catalyst is chosen from platinum, palladium, rhodium, platinum on carbon, palladium on carbon and mixtures thereof.

39. The process of claim 35, wherein the step b) is carried out in the presence of methanol and ammonium formate.

* * * * *